United States Patent [19]

Gitlitz

[11] 4,222,950
[45] * Sep. 16, 1980

[54] METHOD FOR PREPARING TRIORGANOTIN HALIDE

[75] Inventor: Melvin H. Gitlitz, Edison, N.J.

[73] Assignee: M&T Chemicals Inc., Woodbridge, N.J.

[*] Notice: The portion of the term of this patent subsequent to Nov. 15, 1994, has been disclaimed.

[21] Appl. No.: 932,448

[22] Filed: Aug. 10, 1978

Related U.S. Application Data

[63] Continuation of Ser. No. 773,941, Mar. 3, 1977, abandoned.

[51] Int. Cl.² ............................................. C07F 7/22
[52] U.S. Cl. ................................................. 260/429.7
[58] Field of Search ..................................... 260/429.7

[56] References Cited

U.S. PATENT DOCUMENTS

| | | | |
|---|---|---|---|
| 3,297,732 | 1/1967 | Banks | 260/429.7 |
| 3,340,283 | 9/1972 | Gloskey | 260/429.7 |
| 3,355,470 | 11/1967 | Natoli | 260/429.7 |
| 3,402,189 | 9/1968 | Natoli | 260/429.7 |
| 3,607,891 | 9/1971 | Kushlefsky et al. | 260/429.7 |
| 3,647,833 | 3/1972 | Reifenberg et al. | 260/429.7 |
| 3,702,360 | 11/1972 | Graham | 424/288 |
| 3,789,057 | 1/1974 | Reifenberg et al. | 260/429.7 |
| 3,849,460 | 11/1974 | Daniels et al. | 260/429.7 |
| 3,876,795 | 4/1975 | Cracco et al. | 424/288 |
| 4,058,545 | 11/1977 | Gitlitz | 260/429.7 |

FOREIGN PATENT DOCUMENTS

| | | | |
|---|---|---|---|
| 1067437 | 5/1967 | United Kingdom | 260/429.7 |
| 1070942 | 6/1967 | United Kingdom | 260/429.7 |

*Primary Examiner*—Helen M. S. Sneed
*Attorney, Agent, or Firm*—Stanley A. Marcus; Robert Spector

[57] ABSTRACT

Triorganotin compounds of the general formula

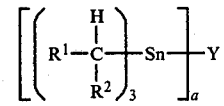

are efficacious insecticides when applied to objects, particularly plants, that are susceptible to infestation by insects. In the foregoing formula $R^1$ and $R^2$ are individually selected from the group consisting of linear and branched-chain alkyl containing from 1 to 4 carbon atoms with the proviso that the total number of carbon atoms in $R^1$ and $R^2$ is from 5 to 7, Y is selected from the group consisting of chlorine, bromine, fluorine, hydroxyl, cyanide, carbamate, thiocarbamate, dithiocarbamate, nitrate, phenoxy, enolate,

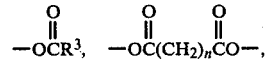

$SR^3$, $OR^4$, oxygen, sulfur, sulfate and phosphate, wherein $R^3$ represents alkyl containing from 1 to 12 carbon atoms or phenyl, $R^4$ is alkyl containing from 1 to 12 carbon atoms, a represents the valence of Y and is the integer 1, 2 or 3 and n represents an integer from 1 to 6, inclusive.

5 Claims, No Drawings

METHOD FOR PREPARING TRIORGANOTIN HALIDE

This is a continuation of application Ser. No. 773,941, filed Mar. 3, 1977.

BACKGROUND OF THE INVENTION

This invention relates to a method for selectively controlling insects using a specified class of triorganotin compounds. The insects against which the compounds are effective are responsible for a considerable portion of the annual damage to agricultural crops. Many tri-n-alkyltin compounds, particularly tri-n-butyltin derivatives may effectively control these insects to some extent, however, these compounds are sufficiently non-selective toward desirable plant crops in that while the insect attacking the plant may be controlled, the plant to which the compound is applied is often killed or severely damaged. Thus, tri-n-alkyltin compounds wherein the hydrocarbon radicals contain from 1 to 4 carbon atoms cannot be employed as pesticides on agricultural crops.

It has now been found that a novel class of tri(sec-alkyl)tin compounds effectively control insects which attack agricultural crops, yet do not seriously damage the plants at the use levels required to control these insects.

SUMMARY OF THE INVENTION

This invention provides a method for controlling insects by applying directly to the insects or to locations susceptible to infestation by these insects a composition consisting essentially of an inert liquid or solid carrier and an insecticidally effective amount of a tri(sec-alkyl)tin compound of the general formula

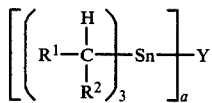

wherein $R^1$ and $R^2$ are individually selected from the group consisting of linear and branched-chain alkyl containing from 1 to 4 carbon atoms with the proviso that the total number of carbon atoms in $R^1$ and $R^2$ is from 5 to 7, Y is selected from the group consisting of chlorine, bromine, fluorine, hydroxyl, cyanide, carbamate, thiocarbamate, dithiocarbamate, nitrate, phenoxy, enolate,

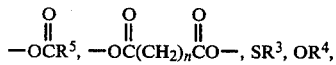

oxygen, sulfur, sulfate and phosphate, wherein $R^3$ represents alkyl containing from 1 to 12 carbon atoms or phenyl, $R^4$ is alkyl containing from 1 to 12 carbon atoms, a represents the valence of Y and is the integer 1, 2 or 3 and n represents an integer from 1 to 6, inclusive.

DETAILED DESCRIPTION OF THE INVENTION

The three hydrocarbon groups of the present triorganotin compounds contain a secondary carbon atom that is bonded to a hydrogen atom and two alkyl groups, each of which contains from 1 to 4 carbon atoms. The remaining valence of the secondary carbon atom is satisfied by a bond to the tin atom. Preferred sec-alkyl groups include 2-pentyl, 3-pentyl, 2-hexyl, 3-hexyl and 4-methyl-2-pentyl.

The tri(sec-alkyl)tin halides wherein the halogen is chlorine, bromine or iodine are prepared by reacting at least three moles of the corresponding sec-alkyl magnesium halide,

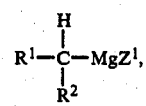

for every mole of an alkyltin trihalide $RSnZ_3{}^2$. The alkyl radical is linear and contains from one to eight carbon atoms.

The resultant tetraorganotin compound,

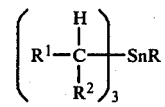

wherein R represents the alkyl residue from the aforementioned alkyltin trihalide is reacted with an equimolar amount of a stannic halide, $SnZ_4{}^3$. During the reaction the lower alkyl residue R present on the tetraorganotin compound is replaced by a halogen atom from the stannic halide. The reactions involved in the formation of the present triorganotin compounds can be represented by the following two equations where $Z^1$, $Z^2$ and $Z^3$ are individually selected from the group consisting of chlorine, bromine and iodine.

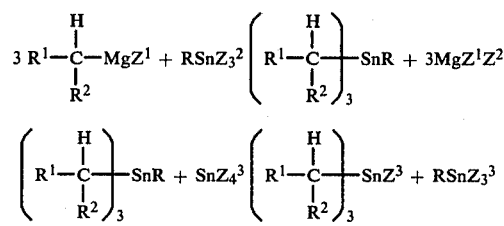

The aforementioned alkyltin trihalide $RSnZ_3{}^2$ can, in turn, be prepared by reacting the corresponding alkyl halide, $RZ^1$, with a stannous halide $SnZ_2{}^1$ as described in U.S. Pat. No. 3,340,283, the pertinent sections of which are hereby incorporated by reference.

It is known to prepare tri(linear aliphatic)tin halides wherein all the organic groups are identical by reacting the corresponding tetra(linear aliphatic)tin compound with an equimolar amount of the desired stannic halide. This process is described in an article R. K. Ingham et al. that appeared in the October, 1960 issue of Chemical Reviews beginning at page 485. This procedure is not feasible for preparing the secondary alkyl compounds of this invention because of decomposition which occurs at the relatively high temperatures required to effect the redistribution reaction using a tetraorganotin compound of the general formula

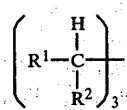

Surprisingly it has now been discovered that if one of the four secondary alkyl groups is replaced by a linear alkyl group, represented by R in the foregoing formula, the R group can be selectively replaced by a halogen atom from a stannic halide. The temperature required to effect this reaction is considerably lower than that required to react a tetra(secalkyl)tin compound. The undesirable decomposition is thereby avoided and the product is obtained in yields of 90% or more.

The reaction between the stannic halide and the asymmetric tetraorganotin compound should be performed under anhydrous conditions at temperatures from about $-25°$ to $80°$ C., preferably from $+25°$ to $80°$ C. in a hydrocarbon solvent. Preferred solvents include pentane, hexane, cyclohexane and benzene.

The stannic halide is dissolved in an organic solvent and the resultant solution is added dropwise to a second solution containing the tetraorganotin compound in the same solvent. The temperature of the reaction mixture is preferably maintained below about $30°$ C. during the addition, which requires about one hour, after which the mixture is heated to a temperature from $35°$ to $80°$ C. The temperature conveniently employed is the boiling point of the reaction mixture. Heating is continued for from about 15 to 60 minutes to ensure complete reaction. The reaction mixture is then allowed to cool to ambient temperature, and extracted with one or more portions of water or aqueous mineral acid. The by-product of the reaction, a monoorganotin trihalide, $RSnZ_3$, is soluble in aqueous media. The desired product remains in the organic phase, and is readily isolated by boiling off the hydrocarbon solvent. No further purification is usually required, however the product can be distilled if desired. The organic layer is freed of any dissolved water following the extraction step. Any of the conventional chemical dehydrating agents are suitable, provided that they will not react with either the triorganotin halide or the hydrocarbon solvent. Preferred drying agents include anhydrous magnesium sulfate, anhydrous sodium sulfate and anhydrous calcium sulfate.

The present triorganotin halides are liquids at ambient temperature. The halides can readily be converted to other derivatives such as the oxide, acetate and sulfate using known reactions. The desired anionic radical can be introduced by reacting the corresponding triorganotin halide, hydroxide or bis(triorganotin)oxide with the reagent indicated in the following table.

| ORGANOTIN DERIVATIVE + | REAGENT + | DESIRED PRODUCT |
| --- | --- | --- |
| Chloride, Bromide or Iodide | Carboxylic acid + acid acceptor, e.g. pyridine | carboxylate, e.g. acetate |
| Chloride, Bromide or Iodide | alkali metal salt of a carboxylic acid | carboxylate, e.g. acetate |
| Chloride, Bromide or Iodide | aqueous solution of alkali metal hydroxide | oxide (or hydroxide) |
| Chloride, Bromide or Iodide | alkali metal alkoxide or alcohol + acid acceptor (e.g. an amine) | alkoxide |
| Chloride, Bromide or Iodide | alkali metal phenoxide or phenol + acid acceptor | phenoxide |
| Chloride, Bromide or Iodide | potassium fluoride or hydrofluoric acid | fluoride |
| Chloride, Bromide or Iodide | alkali metal sulfide | sulfide |
| Chloride, Bromide or Iodide | alkali metal sulfate | sulfate |
| Chloride, Bromide or Iodide | mercaptan + acid acceptor | mercaptide |
| Chloride, Bromide or Iodide | alkali metal cyanate | cyanate |
| Chloride, Bromide or Iodide | alkali metal thiocyanate | thiocyanate |
| Chloride, Bromide or Iodide | alkali metal thiocarbamate | thiocarbamate |
| Chloride, Bromide or Iodide | alkali metal dithiocarbamate | dithiocarbamate |
| Chloride, Bromide or Iodide | phosphoric acid or alkali metal phosphate | phosphate |
| Chloride, Bromide or Iodide | alkali metal dialkyldithio-phosphate | dialkyldithio-phosphate |
| Oxide or Hydroxide | carboxylic acid or anhydride | carboxylate |
| Oxide or Hydroxide | alcohol (or phenol) | alkoxide (or phenoxide) |
| Oxide or Hydroxide | hydrofluoric acid | fluoride |
| Oxide or Hydroxide | dilute (10-25 weight %) aqueous sulfuric acid | sulfate |
| Oxide or Hydroxide | hydrogen sulfide | sulfide |
| Oxide or Hydroxide | alkyl or aryl mercaptan | mercaptide |
| Oxide or Hydroxide | carbon dioxide | carbonate |

| ORGANOTIN DERIVATIVE + | REAGENT + | DESIRED PRODUCT |
|---|---|---|
| Hydroxide | heat to remove water | oxide |

The reaction conditions such as preferred solvents, temperatures and reaction times for preparing the derivatives summarized in the preceding table are known in the art and, therefore, do not require a detailed description in the present specification. A comprehensive treatment of this subject matter together with numerous literature references is contained in an article by R. K. Ingham et al. that appeared in the October, 1960 issue of CHEMICAL REVIEWS (pp. 459–539). The aforementioned derivatives may be liquids or solids at ambient temperature, depending upon the type of substituents represented by Y.

The present tri(sec-alkyl)tin compounds effectively control many types of undesirable insects when applied to living plants that are susceptible to infestation by these insects. The present compounds are particularly effective against insects of the order homoptera, including aphids, and the larval stage of the order lepodoptera, which includes the cabbage looper, corn borer and the bollworm larva. Some of the compounds effectively control the two-spotted spider mite (*Tetrancychus bimaculatus*). A single application of these compounds to living plants or other substrates can provide residual and extended control of many varieties of insects for a considerable period of time, the duration of which is dependent to some extent upon mechanical and biological influences, including weather. Formulations containing the present organotin compounds can be applied directly to the insect to be controlled.

In preparing compositions for application to plants the organotin compound is often augmented or modified by combining it with one or more commonly employed pesticide additives or adjuvants including organic solvents, water or other liquid carriers, surfactants to aid in dispersing or emulsifying the organotin compound or particulate and finely comminuted or divided solid carriers. Depending upon the concentration of triorganotin compound in these compositions, they can be employed either without additional dilution or as liquid concentrates which are subsequently diluted with one or more additional inert liquids to produce the ultimate treating compositions. In compositions employed as concentrates, the triorganotin compound can be present at concentrations of from about 5 to about 98% by weight. Other biologically active agents that are chemically compatible with the present triorganotin compounds can also be added.

The optimum effective concentration of tin compounds to be employed as toxicant in a composition is dependent upon whether the insect is contacted with or ingests the toxicant. The actual weight of compound constituting an effective dose is primarily dependent upon the susceptibility of a particular insect to a given triorganotin compound. For control of the cabbage looper (*Trichoplusia ni*), good results are obtained with liquid or dust compositions containing as little as 25 parts per million by weight of toxicant. Compositions containing up to 90 percent by weight of toxicant can be employed to treat a heavily infested area.

In the preparation of dust compositions, the organotin compound can be blended with many commonly employed finely divided solid carriers such as fuller's earth, attapulgite, bentonite, pyrophyllite, vermiculite, diatomaceous earth, talc, chalk, gypsum and wood flour. The carrier, usually in a finely divided form, is ground or mixed with the toxicant or wetted with a dispersion of the toxicant in a volatile liquid. Depending upon the relative proportions of toxicant and carrier, these compositions can be employed as concentrates that are subsequently diluted with additional solid carrier to obtain the desired amount of active ingredient. Alternatively, such concentrate dust compositions can be employed in combination with various known anionic, cationic or non-ionic surfactants as emulsifying or dispersing agents to form spray concentrates. Such concentrates are readily dispersible in liquid carriers to form spray compositions or liquid formulations containing the toxicants in any desired amount. The choice and concentration of surfactant are determined by the ability of the material to facilitate the dispersing of the concentrate in the liquid carrier to produce the desired liquid composition. Suitable liquid carriers include water, methanol, ethanol, isopropanol, methyl ethyl ketone, acetone, methylene chloride, chlorobenzene, toluene, xylene and petroleum distillates. Among the preferred petrolleum distillates are those boiling under 400° F. at atmospheric pressure and having a flash point above about 80° F.

Liquid compositions can also be prepared by dissolving one of the present triorganotin compounds in a mixture containing a water-immiscible organic liquid and a surface active dispersing agent. The resultant emulsifiable concentrate is then further diluted with water and an oil to form spray mixtures in the form of oil-in-water emulsions. In such compositions, the carrier comprises an aqueous emulsion, i.e. a mixture of water-immiscible solvent, emulsifying agent and water. Preferred dispersing agents for these compositions are oil soluble and include the condensation products of alkylene oxides with phenols and organic and inorganic acids, polyoxyethylene derivatives of sorbitan esters, alkylarylsulfonates, complex ether alcohols, mahogany soaps and the like. Suitable organic liquids to be employed in the compositions include petroleum distillates, hexanol, liquid halohydrocarbons and synthetic organic oils. The surface active dispersing agents are usually employed in the liquid dispersions and aqueous emulsions in the amount of from about 1 to about 20 percent by weight of the combined weight of the dispersing agent and the active toxicant.

When operating in accordance with the present invention, the organotin compound or a composition containing the compound can be applied directly onto the undesirable insect or to the site to be protected, particularly plants and trees. Application to the foliage of plants is conveniently carried out using power dusters, boom sprayers and spray dusters. When employed in this manner the compositions should not contain any significant amounts of phytotoxic diluents. In large scale operations, dusts or low volume sprays may be applied from an aircraft.

The following examples represent preferred embodiments of the present compounds and their use as insecticides, and are not intended to limit the scope of the accompanying claims. All parts and percentages are by weight unless otherwise specified.

EXAMPLES

EXAMPLE 1

Preparation of Tri(3-pentyl)tin Chloride

A. Preparation of Methyl Tri(3-pentyl)tin

To 16 g. (0.66 g. atom) of magnesium turnings maintained at a temperature of 25° C. under a nitrogen atmosphere was added a 25 cc. portion of a solution containing 99.7 g. (0.66 mole) of 3-bromopentane dissolved in 300 cc. of anhydrous tetrahydrofuran. The reaction was initiated using a few drops of ethylene dibromide. The remaining portion of the 3-bromopentane solution was gradually added during a period of one hour while the reaction mixture was heated to the boiling point. Heating was continued for an additional hour. The reaction mixture was then allowed to cool to ambient temperature, at which time all of the magnesium appeared to have reacted. The resultant solution contained 0.6 mole of 3-pentyl magnesium bromide, and was added dropwise to a stirred solution of methyltin trichloride (49 g., 0.2 mole) dissolved in 50 cc. of dry benzene. The addition required 0.5 hour and was conducted under a nitrogen atmosphere. During the addition the temperature of the reaction mixture rose to 71° C. Following completion of the addition the reaction mixture was heated to the boiling point for one hour, then allowed to cool to ambient temperature. To the resultant mixture was added a solution containing 250 cc. water and 15 cc. concentrated sulfuric acid over a five minute period. The aqueous phase was separated and the residual was removed by combining the organic phase with a portion of anhydrous magnesium sulfate, which was subsequently removed by filtration. The solvent was evaporated under reduced pressure to yield 58.8 g. (85% yield) of a yellow liquid exhibiting a refractive index ($n_D^{25}$) of 1.4954. This product was extracted twice with methanol and distilled under reduced pressure. The fraction boiling from 81° to 87° C. under a pressure of 0.15 mm. was isolated and exhibited a refractive index ($n_D^{22}$) of 1.4920. Analysis by vapor phase chromatography indicated that the product was 95.7% pure.

B. Cleavage of Methyl Tri(3-pentyl)tin to Tri(3-pentyl)tin Chloride

A 20.8 g. (0.06 mole) portion of the methyl tri(3-pentyl)tin prepared as described in part A of this example was dissolved in 50 cc. of pentane. To this solution was added a solution containing 15.6 g. (0.06 mole) of stannic chloride and 50 cc. pentane. The addition required 20 minutes, following which the resultant mixture was heated to the boiling point (40° C.) for 45 minutes and then allowed to cool to ambient temperature. A solution obtained by combining 2 cc. of 12 N aqueous hydrochloric acid and 200 cc. water was then added to the reaction mixture with vigorous stirring both during the addition and for three minutes thereafter. The organic layer of the resultant two-phase liquid was isolated and combined with an aqueous hydrochloric acid solution prepared as described hereinabove. The organic layer was again isolated and the water therein removed using a quantity of anhydrous magnesium sulfate. The pentane was then evaporated under reduced pressure to yield 21.6 g. of a yellow liquid exhibiting a refractive index ($n_D^{25}$) of 1.5060. Upon analysis the product was found to contain 32.04% tin and 9.42% chlorine. The calculated values for tri(3-pentyl)tin chloride are 32.29% tin and 9.64% chlorine.

Bis[tri(3-pentyl)tin]oxide was prepared by adding a solution of the corresponding chloride (37.4 g. of the chloride in 100 cc. of a solution containing equal volumes of methanol and ethanol) to a solution containing 16.0 g. of sodium hydroxide, 50 cc. water and 50 cc. methanol. The addition was gradual and required 15 minutes. The resultant cloudy solution was heated to the boiling point for 15 minutes, after which it was allowed to cool to ambient temperature. A 400 cc. portion of water followed by 300 cc. of diethyl ether were added while the mixture was vigorously stirred. The ether layer of the resultant two-phase liquid was freed of water using anhydrous magnesium sulfate, after which the drying agent was removed and the ether evaporated by heating the mixture under reduced pressure. The residual yellow liquid weighed 34.9 g. and was found to contain 34.62% tin and no chlorine. Pure bis[tri(3-pentyl)tin]oxide contains 34.95% tin. Analysis by potentiometric titration indicated that the oxide was 93.4% pure.

EXAMPLE 2

Preparation of Tri(2-pentyl)-, Tri(3-hexyl)- and Tris(4-methyl-2-pentyl)tin Chlorides and Oxides Each of the title compounds were prepared from a corresponding methyl tri(sec-alkyl)tin compound as described in Example 1. The reagents employed and the properties of the intermediate tetraorganotin compound, chloride and oxide are set forth in the following tables.

The aforementioned intermediate tetraorganotin compounds were prepared in the usual manner from methyltin trichloride and the corresponding Grignard reagent in the quantities shown below.

TABLE I

| Preparation of Tetraorganotin Compounds | | | | |
|---|---|---|---|---|
| Product | Grignard Reagent | Moles | MeSpCl₃ (g.) | Prod. Wt. |
| Methyltri(2-pentyl)tin | 2-Pentyl MgBr | 1 | 72 | 68.9 g.* |
| Methyltri(3-hexyl)tin | 3-Hexyl MgBr | 1 | 72 | 69.8 g.* |
| Methyltri(4-methyl-2-(pentyl(tin | 4-Methyl-2-pentyl MgBr | 1 | 72 | 73.3 g.* |

*following distillation

TABLE II

| Intermediate Compound | Properties of Tetraorganotin Compounds | | | | | | | |
|---|---|---|---|---|---|---|---|---|
| | Found | | Theory | | Assay VPC % | B.P. @ Pressure (mm. of Hg.) | | $n_D$ |
| | % Sn | % Cl | % Sn | % Cl | | | | |
| Methyltri (2-pentyl)tin | 34.28 | 0.12 | 34.19 | 0.0 | 96.2 | 88–92 | @ 0.07 | 1.4835 @ 21° C. |
| Methyltri (3-hexyl)tin | 30.25 | 0.65 | 30.50 | 0.0 | 93.6 | 107–114 | @ 0.4 | 1.4904 @ 19° C. |
| Methyltri (4-methyl-2- | 29.28 | 0.11 | 30.50 | 0.0 | 95.1 | 103–107 | @ 0.15 | 1.4765 @ 26° C. |

TABLE II-continued

| | Properties of Tetraorganotin Compounds | | | | | | |
|---|---|---|---|---|---|---|---|
| Intermediate | Found | | Theory | | Assay | B.P. @ Pressure | |
| Compound | % Sn | % Cl | % Sn | % Cl | VPC % | (mm. of Hg.) | $n_D$ |
| pentyl)tin | | | | | | | |

TABLE III

| | Preparation of the Tri(sec-alkyl)tin Chlorides | | | |
|---|---|---|---|---|
| Final Product | Intermediate | Weight (g.) | SnCl$_4$ Wt. (g.) | Product Weight |
| Tri(2-pentyl) tin chloride | Methyltri(2-pentyl)tin | 20.8 | 15.6 | 21.4 g. |
| Tri(3-hexyl) tin chloride | Methyltri(3-hexyl)tin | 68.1 | 45.6 | 70.6 g. |
| Tri(4-methyl-2-pentyl)tin chloride | Methyltri(4-methyl 2-pentyl)tin | 71.6 | 47.9 | 74.6 g. |

TABLE 4

| | Properties of the Tri(sec-alkyl)tin Chlorides | | | | | |
|---|---|---|---|---|---|---|
| | Found | | Theory | | Assay | |
| | % Sn | % Cl | % Sn | % Cl | VPC % | $n_D$ |
| Tri(2-pentyl)tin Chloride | 32.34 | 9.28 | 32.29 | 9.65 | 95.6 | 1.4956 @ 25° C. |
| Tri(3-hexyl)tin Chloride | 28.94 | 8.67 | 28.97 | 8.65 | 95.9 | 1.5005 @ 21° C. |
| Tri(4-methyl-2-pentyl) tin Chloride | 29.02 | 8.70 | 28.97 | 8.65 | 94.2 | 1.4900 @ 23° C. |

The organotin chlorides shown in Table 4 were converted to bis-oxide derivatives in a manner essentially similar to that described above for bis(tri-3-pentyl)tin oxide. Properties of these materials are shown in Table 5 below.

TABLE 5

| | Properties of Bis[tri(sec-alkyl)tin] oxides | | | | | |
|---|---|---|---|---|---|---|
| | Found | | Theory | | Assay* | |
| Product | % Sn | % Cl | % Sn | % Cl | % | $n_D$ |
| Bis[tri(2-pentyl)tin] oxide | 34.58 | 0 | 34.95 | 0 | 99.6 | 1.5000 @ 21° C. |
| Bis[tri(3-hexyl)tin] oxide | 30.90 | 0.01 | 31.06 | 0 | 99.5 | 1.5028 @ 22° C. |
| Bis[tri(4-methyl-2-pentyl)tin] oxide | 30.89 | 0 | 31.06 | 0 | 100 | 1.4914 @ 22° C. |

*by potentiometric titration

EXAMPLE 3

Biological Activity of Tri(sec-alkyl)tin Compounds

The efficacy of five of the compounds disclosed in the foregoing examples in controlling a number of undesirable insects was evaluated using one or more of the test procedures summarized hereinafter.

TEST PROCEDURES

A. The insect is placed in an aqueous dispersion containing a specified concentration of the organotin compound. Contact time is two seconds. The larvae were then set aside for six days, at which time the percent mortality was observed.

B. A bean plant is sprayed with an aqueous dispersion containing a specified concentration of organotin compound. The test insect is placed on the treated foliage and remains undisturbed for three days, at which time the percent mortality is observed.

C. A bean plant infested with the insect is sprayed and remains undisturbed for three days, at which time the percent mortality is observed.

D. Five third instar bollworm larvae are placed in petri plates containing a layer of semi-synthetic diet. These larvae are sprayed with 3 cc. of a solution or suspension containing 400 parts per million (ppm) of the chemical. The spraying is accomplished from a distance of 15 inches (38 cm.) using a Spraying Systems Company nozzle type 40100-120. After spraying, the petri dish cover is replaced with a fiber brewer lid to permit limited air exchange. A mortality count is taken following a holding period of up to three days.

The concentrations of active compound in the following tables are expressed in parts per million (ppm) of total dispersion.

TABLE 6

| Activity Against Cabbage Looper (*Trichoplusia ni*) | | | |
|---|---|---|---|
| Compound | Procedure | % mortality @ X ppm of compound | |
| | | x = 400 | 100 |
| Tri(3-hexyl)tin chloride | A | 100 | 80 |
| | B | 100 | 100 |
| Bis[tri(3-pentyl)tin] oxide | A | 100 | 100 |
| | B | 100 | 100 |
| Bis[tri(2-pentyl)tin] oxide | A | 100 | 100 |
| | B | 100 | 0 |
| Bis[tri(4-methyl-] -pentyl)tin] oxide | A | 100 | 100 |
| | B | 100 | 100 |
| Bis[tri(3-hexyl)tin] oxide | A | 100 | 100 |
| | B | 100 | 100 |

TABLE 7

| Activity Against Aphids Using Procedure C | |
|---|---|
| Compound | % mortality @ 100 ppm of Compound |
| Tri(3-hexyl)tin chloride | 100 |
| Bis[tri(3-penyl)tin] oxide | 100 |
| Bis[tri(4-methyl-2-pentyl)tin] oxide | 100 |
| Bis[tri(3-hexyl)tin] oxide | 100 |

TABLE 8

Activity Against Bollworm Larvae (*Heliophis neae*) Using Procedure D

| Compound | % mortality @ 400 ppm of compound |
| --- | --- |
| Tri(3-hexyl)tin chloride | 80 |
| Bis[tri(3-phenyl)tin] oxide | 80 |
| Bis[tri(2-pentyl)tin] oxide | 60 |
| Bis[tri(4-methyl-2-pentyl)tin] oxide | 60 |
| Bis[tri(3-hexyl)tin] oxide | 100 |

TABLE 9

Activity Against Two-Spotted Spider Mite Using Procedure C With Tricyclohexyltin hydroxide As A Control

| Compound | % mortality rate (ppm compound) | | | | | |
| --- | --- | --- | --- | --- | --- | --- |
|  | 400 | 200 | 100 | 50 | 25 | 12.5 |
| Bis[tri(3-pentyl)tin] oxide | 99 | 99 | 96 | 95 | 94 | 38 |
| Tricyclohexyltin hydroxide | 100 | 100 | 99 | 98 | 55 | 0 |

The foregoing data demonstrate that at concentrations below 50 parts per million the present compounds are superior to tricyclohexyltin hydroxide, a commercial miticide. At a level of 25 parts per million bis[tri(3-pentyl)tin]oxide was almost twice as efficacious as the control. In practical terms, this means that less of the present compounds are required to effectively control spider mites relative to present commercially available triorganotin compounds.

What is claimed is:

1. A method for preparing a triorganotin halide of the general formula

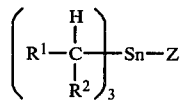

wherein $R^1$ and $R^2$ are individually selected from the group consisting of linear and branched-chain alkyl containing from 1 to 4 carbon atoms with the proviso that the total number of carbon atoms in $R^1$ and $R^2$ is from 5 to 7 and Z is chlorine, bromine or iodine, said method comprising the following steps:

a. reacting a sec-alkylmagnesium halide of of the general formula

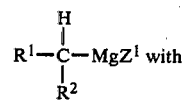

with an alkyltin trihalide of the formula $RSnZ_3^2$ in a molar ratio of 3:1, respectively, to form a tetraorganotin compound

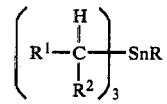

wherein R represents a linear alkyl containing from 1 to 8 carbon atoms and $Z^1$ and $Z^2$ are each individually selected from the group consisting of chlorine, bromine and iodine;

b. reacting said tetraorganotin compound with an equimolar amount of a stannic halide of the general formula $SnZ_4^3$ wherein $Z^3$ is selected from the same group as Z, the reaction of said tetraorganotin compound being conducted under anhydrous conditions and in a hydrocarbon solvent at a temperature of from $-25°$ to $80°$ C.; and c. extracting the resultant reaction mixture containing said triorganotin halide with water or an aqueous solution of a mineral acid to remove the alkyltin trihalide, $RSnZ_3^3$, formed as a by-product of the reaction; and d. removing said hydrocarbon solvent and isolating said triorganotin halide.

2. A method according to claim 1 wherein the temperature of the reaction mixture is maintained below $30°$ C. during the addition of said stannic halide.

3. A method according to claim 2 wherein the reaction mixture is heated to the boiling point following completion of the stannic halide addition.

4. A method according to claim 1 wherein $R^1$ is methyl or ethyl and $R^2$ is ethyl, n-propyl or iso-propyl.

5. A method according to claim 1 wherein said hydrocarbon solvent is selected from the group consisting of pentane, hexane, cyclohexane and benzene.

* * * * *